United States Patent [19]

Atwal

[11] Patent Number: 4,647,561
[45] Date of Patent: Mar. 3, 1987

[54] 1,5-BENZODIAZEPINE COMPOUNDS

[75] Inventor: Karnail Atwal, Cranbury, N.J.

[73] Assignee: E. R. Squibb & Sons, Inc., Princeton, N.J.

[21] Appl. No.: 762,473

[22] Filed: Aug. 5, 1985

[51] Int. Cl.$^4$ .................. C07D 243/12; A61K 31/55
[52] U.S. Cl. .................... 514/221; 540/567;
544/60; 544/111; 544/359; 546/199; 546/148;
546/271; 546/167; 548/523; 548/336; 548/159;
548/217; 548/218; 548/305; 548/465; 549/59;
549/472
[58] Field of Search .................. 260/239 BD, 239 B;
514/221; 544/60, 111, 359; 548/523, 336, 159,
217, 218, 305, 465; 546/199, 271, 148, 167;
549/59, 472

[56] References Cited

FOREIGN PATENT DOCUMENTS 41-18950 11/1966 Japan .......................... 260/239 BD
29385 11/1972 Japan .......................... 260/239 DD

OTHER PUBLICATIONS

Miyano et al., Synthesis of 3,3-Dimethyl-2,3,4,5,10,-11-hexahydro-11-phenyl-1H-dibenzo[b,e][1,-4]-diazepin-1-one, A New Tricyclic System, Chem. Pharm. Bull., 20(7) 1588–89 (1972).
Okamoto et al. "Chem Pharm Bull" (Japan) vol. 29, No. 4, (1981) pp. 1165–1169.

Primary Examiner—Robert T. Bond
Attorney, Agent, or Firm—Lawrence S. Levinson; Stephen B. Davis

[57] ABSTRACT

Compounds of formula

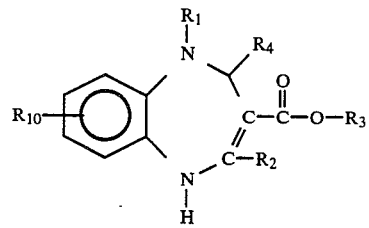

wherein $R_4$ is aryl or heterocyclo are disclosed. These compounds are useful as cardiovascular agents and especially as anti-hypertensive agents.

11 Claims, No Drawings

1,5-BENZODIAZEPINE COMPOUNDS

SUMMARY OF THE INVENTION

This invention relates to the novel 1,5-benzodiazepine compounds of formula I and pharmaceutically acceptable salts thereof

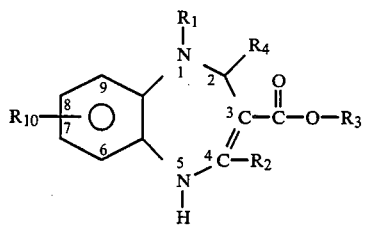
(I)

$R_1$ is hydrogen,

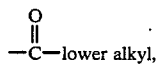

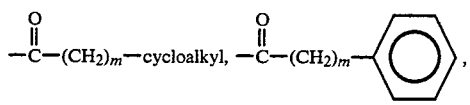

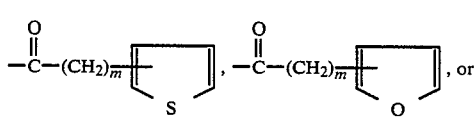, or

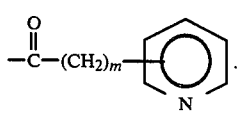

$R_2$ is hydrogen, lower alkyl, lower alkenyl, lower alkynyl, —$(CH_2)_m$-cycloalkyl, —$(CH_2)_m$-aryl, —$(CH_2)_m$-heterocyclo, —$(CH_2)_n$—OH, —$(CH_2)_n$—O-lower alkyl, —$(CH_2)_n$—O—$(CH_2)_m$-aryl, —$(CH_2)_n$—SH, —$CH_2$—S-lower alkyl, —$(CH_2)_n$—S—$(CH_2)_m$-aryl,

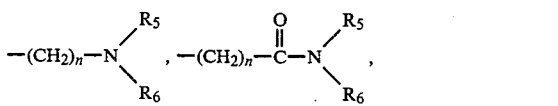

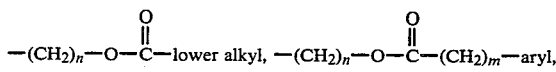

or halo substituted lower alkyl.

$R_3$ is hydrogen, lower alkyl, —$(CH_2)_m$-aryl, —$(CH_2)_m$-cycloalkyl, —$(CH_2)_n$-heterocyclo, —$(CH_2)_p$—OH, —$(CH_2)_p$—O-lower alkyl, —$(CH_2)_p$—O—$(CH_2)_m$-aryl, —$(CH_2)_p$—SH, —$(CH_2)_p$—S-lower alkyl, —$(CH_2)_p$—S—$(CH_2)_m$-aryl,

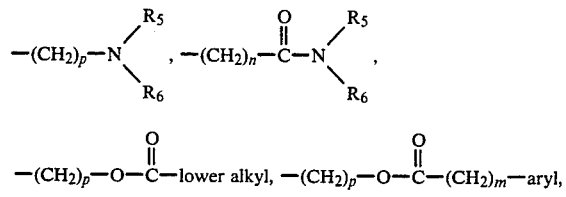

halo substituted lower alkyl, or a pharmaceutically acceptable salt forming ion.

$R_4$ is aryl or heterocyclo.

$R_5$ and $R_6$ are independently selected from the group consisting of hydrogen, lower alkyl,

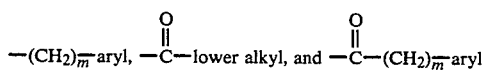

or $R_5$ and $R_6$ taken together with the N atom to which they are attached complete a heterocyclic ring of the formula

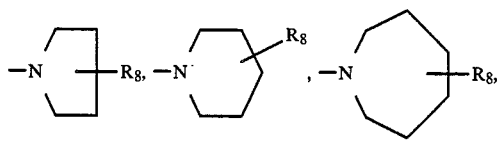

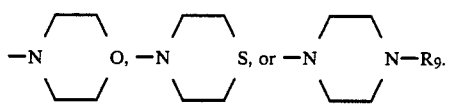

$R_7$ is hydrogen, lower alkyl, —$(CH_2)_m$-aryl, or a pharmaceutically acceptable salt forming ion.
$R_8$ is hydrogen, lower alkyl of 1 to 4 carbons, lower alkoxy of 1 to 4 carbons, lower alkylthio of 1 to 4 carbons, halo, $CF_3$ or hydroxy.
$R_9$ is hydrogen or lower alkyl of 1 to 4 carbons.
m is zero or an integer from 1 to 6.
n is an integer from 1 to 6.
p is an integer from 2 to 6.
$R_{10}$ is hydrogen, lower alkyl of 1 to 4 carbons, lower alkoxy of 1 to 4 carbons, halo, or $CF_3$.

DETAILED DESCRIPTION OF THE INVENTION

This invention in its broadest aspects relates to the 1,5-benzodiazepine compounds of formula I above, to compositions and the method of using such compounds as cardiovascular agents.

The term lower alkyl used in defining various symbols refers to straight or branched chain hydrocarbon radicals having up to eight carbons, preferably from one to five carbons. Similarly, the terms lower alkoxy and lower alkylthio refer to such lower alkyl groups attached to an oxygen or sulfur.

The term lower alkenyl refers to straight or branched chain hydrocarbon radicals having from two to eight carbons and one double bond, preferably three to five carbons. The term lower alkynyl refers to straight or branched chain hydrocarbon radicals having from two to eight carbons and one triple bond, preferably three to five carbons.

The term cycloalkyl refers to saturated rings of 4 to 7 carbon atoms with cyclopentyl and cyclohexyl being most preferred.

The term halo refers to chloro, bromo and fluoro.

The term halo substituted lower alkyl refers to such lower alkyl groups described above in which one or more hydrogens have been replaced by chloro, bromo or fluoro groups such as trifluoromethyl, which is preferred, pentafluoroethyl, 2,2,2-trichloroethyl, chloromethyl, bromomethyl, etc.

The term aryl refers to phenyl, 1-naphthyl, 2-naphthyl, mono substituted phenyl, 1-naphthyl, or 2-naphthyl wherein said substituent is lower alkyl of 1 to 4 carbons, lower alkylthio of 1 to 4 carbons, lower alkoxy of 1 to 4 carbons, halo, nitro, cyano, hydroxy, amino, —NH-alkyl wherein alkyl is of 1 to 4 carbons, —N(alkyl)$_2$ wherein alkyl is of 1 to 4 carbons, CF$_3$, NCS, OCHF$_2$,

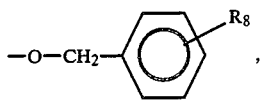

—O—CH$_2$-cycloalkyl,

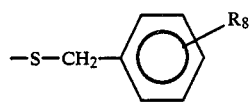

or —S—CH$_2$-cycloalkyl, di- or tri- substituted phenyl 1-naphthyl, or 2-naphthyl wherein said substituents are selected from methyl, methoxy, methylthio, halo, CF$_3$, nitro, hydroxy, amino, and OCHF$_2$, and pentafluorophenyl.

The term heterocyclo refers to fully saturated or unsaturated rings of 5 or 6 atoms containing one or two O and S atoms and/or one to four N atoms provided that the total number of hetero atoms in the ring is 4 or less. The hetero ring is attached by way of an available carbon atom. Preferred monocyclic hetero groups include 2- and 3-thienyl, 2- and 3-furyl, 2-, 3- and 4-pyridyl, and imidazolyl. The term hetero also includes bicyclic rings wherein the five or six membered ring containing O, S and N atoms as defined above is fused to a benzene ring and the bicyclic ring is attached by way of an available carbon atom in the benzene ring. Preferred bicyclic hetero groups include 4, 5, 6, or 7-indolyl, 4, 5, 6, or 7-isoindolyl, 5, 6, 7 or 8-quinolinyl, 5, 6, 7 or 8-isoquinolinyl, 4, 5, 6, or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofurazanyl.

The term heterocyclo also includes such monocyclic and bicyclic rings wherein an available carbon atom is substituted with a lower alkyl of 1 to 4 carbons, lower alkylthio of 1 to 4 carbons, lower alkoxy of 1 to 4 carbons, halo, nitro, keto, cyano, hydroxy, amino, —NH-alkyl wherein alkyl is of 1 to 4 carbons, —N(alkyl)$_2$ wherein alkyl is of 1 to 4 carbons, CF$_3$, NCS, or OCHF$_2$ or such monocyclic and bicyclic rings wherein two or three available carbons have substituents selected from methyl, methoxy, methylthio, halo, CF$_3$, nitro, hydroxy, amino, and OCHF$_2$.

The compounds of formula I wherein R$_1$ is hydrogen can be prepared as follows. A 3-[(2-aminophenyl)amino]-2-alkenoic acid ester of the formula

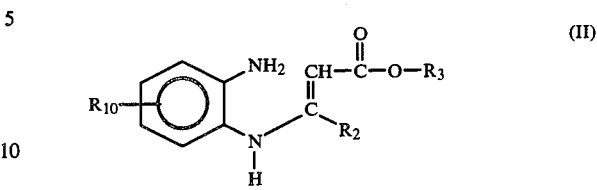

is treated in a suitable solvent with an aldehyde of the formula

R$_4$CHO (III)

in the presence of acetic acid and heat.

The intermediate of formula II is prepared by treating 1,2-benzenediamine of the formula

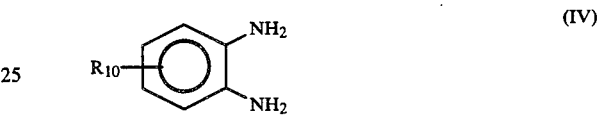

with the β-keto ester of the formula

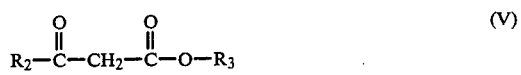

in a suitable solvent in the presence of acetic acid and heat.

The compounds of formula I wherein R$_1$ is

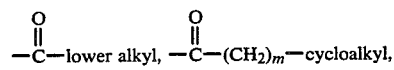

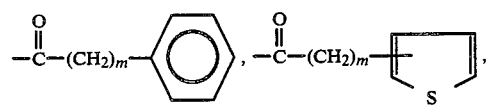

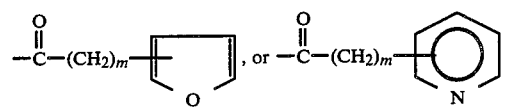

can be prepared by treating the corresponding compound of formula I wherein R$_1$ is hydrogen with an anhydride of the formula

R$_1$—O—R$_1$ (VI)

or an acid chloride of the formula

R$_1$—Cl (VII)

wherein R$_1$ is

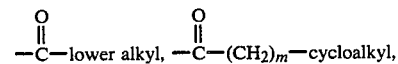

-continued

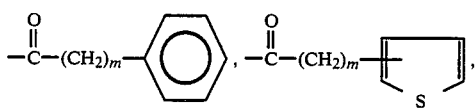, 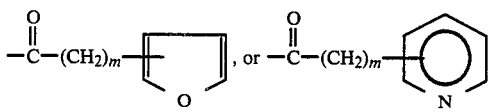,

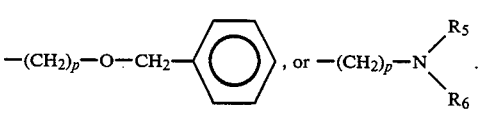

in the presence of pyridine.

If any of $R_2$, $R_3$, $R_4$, $R_5$ and $R_6$ in the above reactions are aryl or —$(CH_2)_m$-aryl wherein aryl is phenyl, 1-naphthyl or 2-naphthyl substituted with one or more hydroxy or amino groups, heterocyclo or —$(CH_2)_n$-heterocyclo wherein the heterocyclo ring contains an NH such as imidazolyl, or a substituted alkyl such as —$(CH_2)_n$—OH, —$(CH_2)_p$—OH, —$(CH_2)_p$—NH$_2$, —$(CH_2)_n$—SH, —$(CH_2)_p$—SH, or

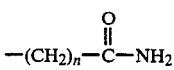

then the hydroxyl, amino, or mercaptan function should be protected during the reaction. Suitable protecting groups include benzyloxycarbonyl, t-butoxycarbonyl, benzyl, benzhydryl, etc. The protecting group is removed by hydrogenation, treatment with acid, or by other known means following completion of the reaction.

Preferred compounds of this invention are those wherein:

$R_1$ is hydrogen or

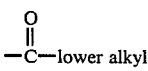

wherein lower alkyl is straight or branched chain of 1 to 4 carbons.

$R_2$ is straight or branched chain lower alkyl of 1 to 5 carbons, especially methyl.

$R_3$ is straight or branched chain lower alkyl of 1 to 5 carbons, —$(CH_2)_p$—O-lower alkyl wherein lower alkyl is straight or branched chain of 1 to 5 carbons,

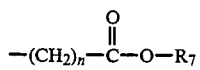

p is 2,3 or 4.

$R_5$ and $R_6$ are independently selected from hydrogen, straight or branched chain lower alkyl of 1 to 5 carbons, and benzyl.

$R_4$ is phenyl, 2-, 3- or 4- mono substituted phenyl wherein said substituent is lower alkyl of 1 to 4 carbons, lower alkoxy of 1 to 4 carbons, lower alkylthio of 1 to 4 carbons, halo, CF$_3$, nitro, or OCHF$_2$, 2,3-disubstituted phenyl, 2,6-disubstituted phenyl, 2,3,4-trisubstituted phenyl or 3,4,5-trisubstituted phenyl wherein said phenyl substitutents are selected from methyl, methoxy, methylthio, halo, CF$_3$, nitro and OCHF$_2$, or pentafluorophenyl.

$R_{10}$ is hydrogen, methyl, methoxy, chloro, or CF$_3$.

Most preferred are the above compounds wherein:

$R_1$ is hydrogen or

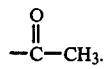

$R_2$ is methyl.

$R_3$ is methyl or ethyl.

$R_4$ is 2-nitrophenyl, 3-nitrophenyl, 2-(trifluoromethyl)phenyl, 2,6-dichlorophenyl, or 2,3-dichlorophenyl.

$R_{10}$ is hydrogen.

The compounds of formula I form salts with a variety of inorganic and organic acids. The non-toxic pharmaceutically acceptable salts are preferred, although other salts may also be useful in isolating or purifying the product. Such pharmaceutically acceptable salts include those formed with hydrochloric acid, methanesulfonic acid, sulfuric acid, acetic acid, maleic acid, etc. The salts are obtained by reacting the product with an equivalent amount of the acid in a medium in which the salt precipitates.

In addition, the compounds of formula I in which $R_2$ or $R_3$ is $$-(CH_2)_n-\overset{O}{\underset{\|}{C}}-O-R_7$$

or in which $R_3$ is hydrogen include carboxylic acid salts, i.e., $R_3$ or $R_7$ is a pharmaceutically acceptable salt forming ion. Preferred salt forming ions include alkali metal salt ions such as sodium, potassium and lithium, and alkaline earth metal salt ions such as calcium and magnesium.

The compounds of formula I and the pharmaceutically acceptable salts thereof are useful as cardiovascular agents. These compounds act as calcium entry blocking vasodilators and are especially useful as anti-hypertensive agents. Thus, by the administration of a composition containing one (or a combination) of the compounds of this invention the blood pressure of a hypertensive mammalian (e.g., human) host is reduced. A single dose, or preferably two to four divided daily doses, provided on a basis of about 0.1 to 100 mg. per kilogram of body weight per day, preferably from about 1 to about 50 mg. per kilogram per day, is appropriate to reduce blood pressure. The substance is preferably administered orally, but parenteral routes such as the subcutaneous, intramuscular, or intravenous routes can also be employed.

As a result of the calcium entry blocking activity of the compounds of formula I, it is believed that such compounds in addition to being anti-hypertensives may also be useful as anti-arrhythmic agents, as anti-anginal agents, as anti-fibrillatory agents, as anti-asthmatic agents, and in limiting myocardial infarction.

The compounds of this invention can also be formulated in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril.

The compounds of formula I can be formulated for use in the reduction of blood pressure in compositions such as tablets, capsules or elixirs for oral administration, or in sterile solutions or suspensions for parenteral administration. About 10 to 500 mg. of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention. Temperatures are given in degrees centigrade.

EXAMPLE 1

2,5-Dihydro-4-methyl-2-(3-nitrophenyl)-1H-1,5-benzodiazepine-3-carboxylic acid, methyl ester A solution of methylacetoacetate (2.32 g., 20 mmole) in absolute ethanol (10 ml.) is treated with 1,2-benzenediamine (2.04 g., 20 mmole). The resulting reaction mixture is heated under reflux for 24 hours. The reaction is cooled to room temperature and treated with 3-nitrobenzaldehyde (3.0 g., 20 mmole) and acetic acid (100 μl.). After stirring at room temperature overnight, the reaction is filtered to remove a yellow solid (1.01 g.) by-product. The mother liquor is concentrated to give an orange oil which is purified by flash chromatography (15–20% acetone in hexane) to provide a yellow roam (2.1 g.). Trituration with dichloromethane-isopropyl ether furnishes 1.21 g. of product as light orange crystals. Recrystallization from dichloromethaneisopropyl ether gives analytically pure 2,5-dihydro-4-methyl-2-(3-nitrophenyl)-1H-1,5-benzodiazepine-3-carboxylic acid, methyl ester; m.p. 124°–126°. TLC (silica gel; ethyl acetate:hexane, 50:50) $R_f=0.32$.

Anal. calc'd. for $C_{18}H_{17}N_3O_4$: C, 63.71; H, 5.05; N, 12.38 Found: C, 63.56; H, 5.12; N, 12.40.

EXAMPLE 2

2,5-Dihydro-4-methyl-2-[2-(trifluoromethyl)phenyl]-1H-1,5-benzodiazepine-3-carboxylic acid, methyl ester (a) 3-[(2-Aminophenyl)amino]-2-butenoic acid, methyl ester A solution containing 1,2-benzenediamine (6.12 g., 60.0 mmole), methylacetoacetate (6.96 g., 60.0 mmole), and acetic acid (0.2 ml.) in benzene (40 ml.) is heated under reflux for 5 hours using a water separator. The reaction is allowed to cool down to room temperature and the solvent is stripped off to provide a brown oil. This oil is dissolved in isopropyl ether and allowed to stand at 5° overnight. An off-white precipitate forms and is filtered off (2:1 g. of by-product). The filtrate is concentrated and the residue is triturated with hexane to give 6.7 g. of 3-[(2-aminophenyl)amino]-2-butenoic acid, methyl ester as a light yellow solid.

(b) 2,5-Dihydro-4-methyl-2-[2-(trifluoromethyl)phenyl]-1H-1,5-benzodiazepine-3-carboxylic acid, methyl ester A solution of 3-[(2-aminophenyl)amino]-2-butenoic acid, methyl ester (2.50 g., 12.0 mmole) in anhydrous tetrahydrofuran (12 ml.) is treated with 2-(trifluoromethyl)benzaldehyde (1.74 g., 10.0 mmole) and acetic acid (0.2 ml.). The resulting reaction mixture is stirred at room temperature under argon for 24 hours. The solvent is removed and the resulting yellow solid is triturated with isopropyl ether to give 3.27 g. of an off-white product. Recrystallization from dichloromethane-isopropyl ether gives 2.39 g. of 2,5-dihydro-4-methyl-2-2-(trifluoromethyl)phenyl]-1H-1,5-benzodiazepine-3-carboxylic acid, methyl ester; m.p. 190°–192°. TLC (silica gel; acetone:hexanes, 35:65) $R_f=0.47$.

Anal. calc'd. for $C_{19}H_{17}F_3N_2O_2$: C, 62.98; H, 4.73; N, 7.73; F, 15.73 Found: C, 63.06; H, 4.84; N, 7.63; F, 15.90.

EXAMPLE 3

2,5-Dihydro-4-methyl-2-(2-nitrophenyl)-1H-1,5-benzodiazepine-3-carboxylic acid, methyl ester A reaction mixture containing 3-[(2-aminophenyl)amino]-2-butenoic acid, methylester (2.5 g., 12.0 mmole), 2-nitrobenzaldehyde (1.51 g., 10.0 mmole), and acetic acid (0.2 ml.) in anhydrous tetrahydrofuran (12 ml.) is stirred at room temperature for about 60 hours. The solvent is stripped off to provide a red solid. This solid is triturated with isopropyl ether and filtered off to give 3.4 g. of an orange solid. This material is purified by flash chromatography (5% ethyl acetate in dichloromethane) and the resulting product is recrystallized from dichloromethane-isopropyl ether to give 1.9 g. of product. The mother liquor is recrystallized again from dichloromethane-isopropyl ether to give a second crop (800 mg.) resulting in a total of 2.7 g. of 2,5-dihydro-4-methyl-2-(2-nitrophenyl)-1H-1,5-benzodiazepine-3-carboxylic acid, methyl ester; m.p. 190°–192°. TLC (silica gel; acetone:hexanes, 35:65) $R_f=0.32$.

Anal. calc'd. for $C_{18}H_{17}N_3O_4$: C, 63.71; H, 5.05; N, 12.38 Found: C, 63.46; H, 4.92; N, 12.14.

EXAMPLE 4

2-(2,3-Dichlorophenyl)-2,5-dihydro-4-methyl-1H-1,5-benzodiazepine-3-carboxylic acid, methyl ester A solution of 3-[(2-aminophenyl)amino]-2-butenoic acid, methyl ester (1.25 g., 6.07 mmole) in anhydrous tetrahydrofuran (10 ml.) and acetic acid (0.1 ml.) is treated with 2,3-dichlorobenzaldehyde (1.06 g., 6.07 mmole). The reaction is allowed to stir overnight at room temperature. The solvent is stripped off to give a brown residue which is triturated with isopropyl ether and filtered off (720 mg.). Recrystallization from absolute ethanol provides 501 mg. of 2-(2,3-dichlorophenyl)-2,5-dihydro-4-methyl-1H-1,5-benzodiazepine-3-carboxylic acid, methyl ester; m.p. 181°–182°. TLC (silica gel; hexanes:ethyl acetate, 60:40) $R_f=0.35$.

Anal. calc'd. for $C_{18}H_{16}Cl_2N_2O_2$: C, 59.52; H, 4.44; N, 7.71; Cl, 19.52 Found: C, 59.67; H, 4.47; N, 7.66; Cl, 19.36.

EXAMPLE 5

2-(2,6-Dichlorophenyl)-2,5-dihydro-4-methyl-1H-1,5-benzodiazepine-3-carboxylic acid, methyl ester A solution of 3-[(2-aminophenyl)amino]-2-butenoic acid, methyl ester (4.74 g., 230 mmole) in anhydrous tetrahydrofuran (20 ml.) and acetic acid (0.2 ml.) is treated with 2,6-dichlorobenzaldehyde (4.03 g., 23.0 mmole). The resulting reaction mixture is stirred at room temperature for 4 days. The solvent is stripped off to give a brown oil which is dissolved in isopropyl ether and allowed to stand at 0°–5° (refrigerator) for 24 hours. The solid that precipitates is filtered off and washed with additional isopropyl ether. This product is triturated with isopropyl ether and filtered off to give 2-(2,6-dichlorophenyl)-2,5-dihydro-4-methyl-1H-1,5-benzodiazepine-3-carboxylic acid, methyl ester; 119°–120° (with decomposition). TLC (silica gel; ethyl acetate:-hexanes, 40:60) $R_f$=0.38.

Anal. calc'd. for $C_{18}H_{16}Cl_2N_2O_2$: C, 59.52; H, 4.44; N, 7.71; Cl, 19.52 Found: C, 59.29; H, 4.45; N, 7.43; Cl, 19.41.

EXAMPLES 6–26

Following the procedure of Examples 1 to 5, the 1,2-benzenediamine shown below in Col. I is reacted with the ester shown in Col. II to give the intermediate shown in Col. III. Treatment with the aldehyde shown below in Col. IV gives the product shown in Col. V.

Col. I

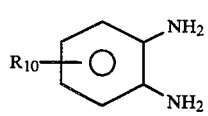

Col. II

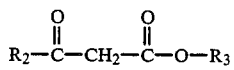

Col. III

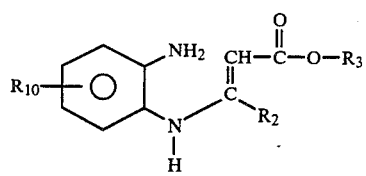

Col. IV $R_4$—CHO

Col. V

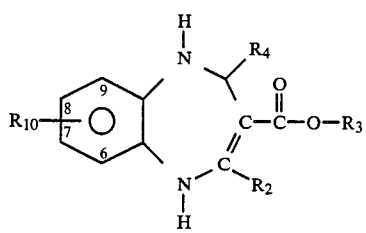

| Example | $R_{10}$ | $R_2$ | $R_3$ | $R_4$ |
|---|---|---|---|---|
| 6 | —Cl(8-position) | —CH₃ | —CH₃ | phenyl-CF₃ |
| 7 | —CH₃(8-position) | —CH₃ | —C₂H₅ | phenyl-NO₂ |
| 8 | —OCH₃(8-position) | —CH₃ | —CH₃ | phenyl-NO₂ |
| 9 | —CF₃(8-position) | —CH₃ | —CH₃ | phenyl-Cl,Cl |
| 10 | —Cl(7-position) | —CH₃ | —CH₃ | phenyl-NO₂,Cl |
| 11 | —H | —CH₃ | —(CH₂)₂—O—CH₂—phenyl | pentafluorophenyl |

-continued

| Example | R₁₀ | R₂ | R₃ | R₄ |
|---|---|---|---|---|
| 12 | —H | —CH₃ | —(CH₂)₂—N(CH₃)—CH₂—C₆H₅ | 2-nitrophenyl |
| 13 | —H | —CH₃ | —C₂H₅ | 6-nitronaphthyl |
| 14 | —H | —CH₃ | —CH₂—CH(CH₃)₂ | 6-(trifluoromethyl)naphthyl |
| 15 | —H | —CH₃ | —CH₃ | 2-(methylthio)pyridinyl |
| 16 | —H | —CH₃ | —(CH₂)₂—S—CH₃ | thienyl |
| 17 | —H | —CH₃ | —(CH₂)₂—S—C₆H₅ | 1-benzylimidazolyl |
| 18 | —H | —CH₃ | —(CH₂)₂—N(CH₃)₂ | 1-benzylindolyl |
| 19 | —Cl(8-position) | —CH₃ | —CH₂—C(O)—N(CH₃)₂ | isoindolyl |
| 20 | —H | —CH₂—C₆H₅ | —CH₃ | quinolinyl |
| 21 | —Cl(8-position) | —CF₃ | —C₂H₅ | isoquinolinyl |

-continued
| Example | R₁₀ | R₂ | R₃ | R₄ |
|---|---|---|---|---|
| 12 | —H | —CH₃ | —(CH₂)₂—N(CH₃)(CH₂C₆H₅) | 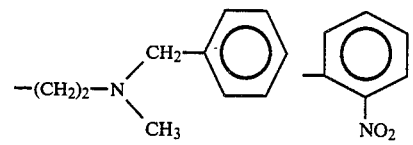 2-nitrophenyl |
| 13 | —H | —CH₃ | —C₂H₅ | 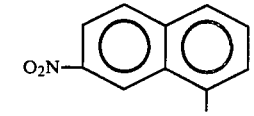 6-nitro-naphthyl |
| 14 | —H | —CH₃ | —CH₂—CH—(CH₃)₂ | 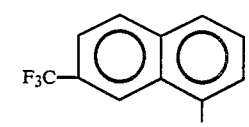 6-trifluoromethyl-naphthyl |
| 15 | —H | —CH₃ | —CH₃ | 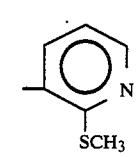 2-methylthio-pyridyl |
| 16 | —H | —CH₃ | —(CH₂)₂—S—CH₃ | 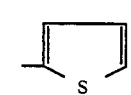 thienyl |
| 17 | —H | —CH₃ | —(CH₂)₂—S—C₆H₅ | 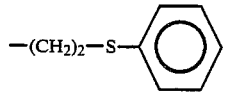 1-benzyl-imidazolyl |
| 18 | —H | —CH₃ | —(CH₂)₂—N(CH₃)₂ | 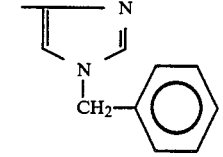 1-benzyl-indolyl |
| 19 | —Cl(8-position) | —CH₃ | —CH₂—C(O)—N(CH₃)₂ | 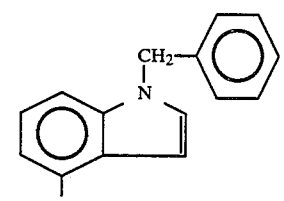 isoquinolinyl |
| 20 | —H | —CH₂—C₆H₅ | —CH₃ | 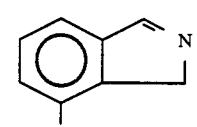 quinolinyl |
| 21 | —Cl(8-position) | —CF₃ | —C₂H₅ | 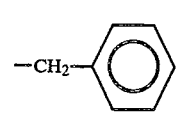 isoquinolinyl |

| Example | R10 | R2 | R3 | R4 |
|---|---|---|---|---|
| 22 | —H | —CH$_2$—O—CH$_3$ | —CH$_3$ | benzothiazole-type ring |
| 23 | —H | —CH$_2$—O—C$_6$H$_5$ | —(CH$_2$)$_2$—N(piperidine) | benzoxazole-type ring |
| 24 | —H | —CH$_2$—S—C$_2$H$_5$ | —CH$_3$ | N-benzyl benzimidazole-type ring |
| 25 | —H | —CH$_2$—S—CH$_2$—C$_6$H$_5$ | —CH$_3$ | benzo-oxadiazole-type ring |
| 26 | —H | —CH$_3$ | —(CH$_2$)$_2$—N(N-methylpiperazine) | benzo-oxadiazine-type ring |

The N-protecting group in Examples 17, 18 and 24 are removed as the last step in the synthesis.

EXAMPLE 27

1-Acetyl-2,5-dihydro-4-methyl-2-(3-nitrophenyl)-1H-1,5-benzodiazepine-3-carboxylic acid, methyl ester A solution of 2,5-dihydro-4-methyl-2-(3-nitrophenyl)-1H-1,5-benzodiazepine-3-carboxylic acid, methyl ester (800 mg., 2.36 mmole) in dichloromethane (8 ml.) is treated with pyridine (280 mg., 3.53 mmole), acetic anhydride (479 mg., 4.72 mmole) and 4-dimethylaminopyridine (5 mg.). The reaction is stirred at room temperature for 16 hours. A light yellow solid precipitates out of the reaction. The reaction is diluted with dichloromethane/methanol (100 ml. of 95:5 mixture) and the resulting solution is washed with 10% citric acid, 5% sodium bicarbonate, and brine. After drying over anhydrous magnesium sulfate, the solvent is evaporated to give a yellow foam. This foam is triturated with ether to give 705 mg. of yellow crystals. Recrystallization from dichloromethane-methanol-isopropanol gives an analytically pure sample of 1-acetyl-2,5-dihydro-4-methyl-2-(3-nitrophenyl)-1H-1,5-benzodiazepine-3-carboxylic acid, methyl ester as yellow crystals; m.p. 231°–232.5°. TLC(silica gel; acetone:hexane, 40:60) R$_f$=0.28.

Anal. calc'd. for C$_{20}$H$_{19}$N$_3$O$_5$: C, 62.99; H, 5.02; N, 11.02 Found: C, 63.02; H, 5.15; N, 11.07.

Similarly, by reacting the products of Examples 2 to 26 with acetic anhydride according to the above procedure other compounds within the scope of the invention are obtained.

EXAMPLES 28–37

Following the procedure of Example 27 but substituting the acid chloride shown below in Col. I for the acetic anhydride one obtains the product shown in Col. II.

Col. I
R$_1$—Cl

Col. II

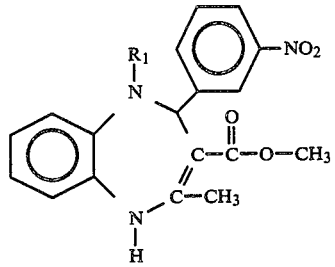

| Example | R$_1$ |
|---|---|
| 28 | —C(O)—C$_2$H$_5$ |
| 29 | —C(O)—C$_3$H$_7$ |

-continued

| | Col. I |
|---|---|
| | R₁—Cl |
| | Col. II |

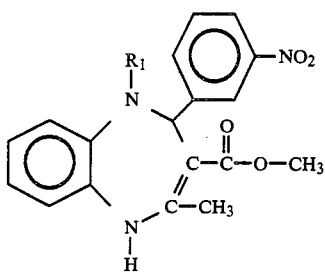

| Example | R₁ |
|---|---|
| 30 | —C(=O)—C₆H₅ (phenyl) |
| 31 | —C(=O)—CH₂—C₆H₅ |
| 32 | —C(=O)—CH₂—(2-thienyl) |
| 33 | —C(=O)—CH₂—(2-furyl) |
| 34 | —C(=O)—(CH₂)₂—(2-pyridyl) |
| 35 | —C(=O)—CH₂—(3-pyridyl) |
| 36 | —C(=O)—CH₂—cyclohexyl |
| 37 | —C(=O)—(CH₂)₃—cyclopentyl |

EXAMPLE 38

1000 tablets each containing the following ingredients:

| | | |
|---|---|---|
| 2,5-Dihydro-4-methyl-2-(3-nitrophenyl)-1H—1,5-benzodiazepine-3-carboxylic acid, methyl ester | 100 | mg. |
| Cornstarch | 50 | mg. |
| Gelatin | 7.5 | mg. |
| Avicel (microcrystalline cellulose) | 25 | mg. |
| Magnesium stearate | 2.5 | mg. |
| | 185 | mg. | are prepared from sufficient bulk quantities by mixing the 2,5-dihydro-4-methyl-2-(3-nitrophenyl)-1H-1,5-benzodiazepine-3-carboxylic acid, methyl ester and cornstarch with an aqueous solution of the gelatin. The mixture is dried and ground to a fine powder. The Avicel and then the magnesium stearate are admixed with granulation. This mixture is then compressed in a tablet press to form 1000 tablets each containing 100 mg. of active ingredient.

In a similar manner, tablets containing 100 mg. of the product of any of Examples 2 to 37 can be prepared.

A similar procedure can be employed to form tablets containing 50 mg. of active ingredient.

EXAMPLE 39

Two piece #1 gelatin capsules are filled with a mixture of the following ingredients:

| | | |
|---|---|---|
| 2,5-Dihydro-4-methyl-2-[2-(trifluoromethyl)phenyl]-1H—1,5-benzodiazepine-3-carboxylic acid, methyl ester | 50 | mg. |
| Magnesium stearate | 7 | mg. |
| Lactose | 193 | mg. |
| | 250 | mg |

In a similar manner capsules containing 50 mg. of the product of any of Examples 1 and 3 to 37 can be prepared.

EXAMPLE 40

An injectable solution is prepared as follows:

| | | |
|---|---|---|
| 2,5-Dihydro-4-methyl-2-(2-nitrophenyl)-1H—1,5-benzodiazepine-3-carboxylic acid, methyl ester | 500 | g. |
| Methyl paraben | 5 | g. |
| Propyl paraben | 1 | g. |
| Sodium chloride | 25 | g. |
| Water for injection | 5 | l. |

The active substance, preservatives, and sodium chloride are dissolved in 3 liters of water for injection and then the volume is brought up to 5 liters. The solution is filtered through a sterile filter and aseptically filled into presterilized vials which are closed with presterilized rubber closures. Each vial contains 5 ml. of solution in a concentration of 100 mg. of active ingredient per ml. of solution for injection.

In a similar manner, an injectable solution containing 100 mg. of active ingredient per ml. of solution can be prepared for the product of any of Examples 1, 2 and 4 to 37.

EXAMPLE 41

1000 tablets each containing the following ingredients:

| | | |
|---|---|---|
| 1-Acetyl-2,5-dihydro-4-methyl-2-(3-nitrophenyl)-1H—1,5-benzodiazepine-3-carboxylic acid, methyl ester | 100 | mg. |
| Avicel | 100 | mg. |

-continued

| | | |
|---|---:|---|
| Hydrochlorothiazide | 12.5 | mg. |
| Lactose | 113 | mg. |
| Cornstarch | 17.5 | mg. |
| Stearic acid | 7 | mg. |
| | 350 | mg. | are prepared from sufficient bulk quantities by slugging the 1-acetyl-2,5-dihydro-4-methyl-2-(3-nitrophenyl)-1H-1,5-benzodiazepin-3-carboxylic acid, methyl ester, Avicel, and a portion of the stearic acid. The slugs are ground and passed through a #2 screen, then mixed with the hydrochlorothiazide, lactose, cornstarch, and remainder of the stearic acid. The mixture is compressed into 350 mg. capsule shaped tablets in a tablet press. The tablets are scored for dividing in half.

In a similar manner, tablets can be prepared containing 100 mg. of the product of any of Examples 1 to 26 and 28 to 37.

What is claimed is:

1. A compound of the formula:

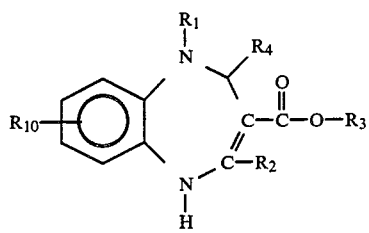

including a pharmaceutically acceptable salt thereof wherein:

$R_1$ is hydrogen,

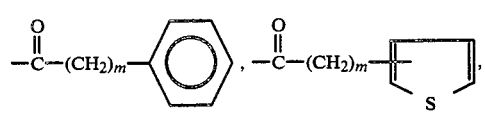

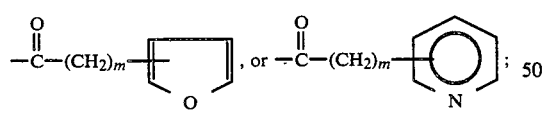

$R_2$ is hydrogen, lower alkyl, lower alkenyl, lower alkynyl, $-(CH_2)_m$-cycloalkyl, $-(CH_2)_m$-aryl, $-(CH_2)_m$-heterocyclo, $-(CH_2)_n$-OH, $-(CH_2)_n$-O-lower alkyl, $-(CH_2)_n$-O-$(CH_2)_m$-aryl, $-(CH_2)_n$-SH, $-CH_2$-S-lower alkyl, $-(CH_2)_n$-S-$(CH_2)_m$-aryl,

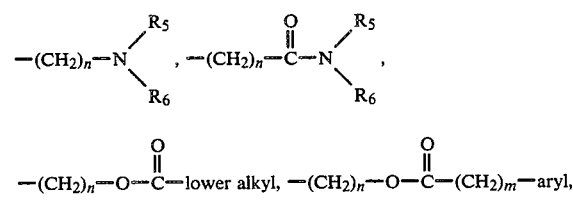

or halo substituted lower alkyl;

$R_3$ is hydrogen, lower alkyl, $-(CH_2)_m$-aryl, $-(CH_2)_m$-cycloalkyl, $-(CH_2)_n$-heterocyclo, $-(CH_2)_p$-OH, $-(CH_2)_p$-O-lower alkyl, $-(CH_2)_p$-O-$(CH_2)_m$-aryl, $-(CH_2)_p$-SH, $-(CH_2)_n$-S-lower alkyl, $-(CH_2)_p$-S-$(CH_2)_m$-aryl,

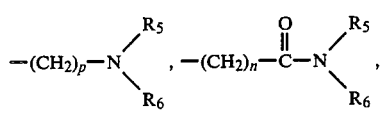

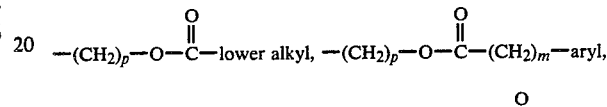

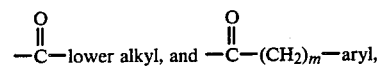

halo substituted lower alkyl, or a pharmaceutically acceptable salt forming ion;

$R_4$ is aryl or heterocyclo;

$R_5$ and $R_6$ are independently selected from the group consisting of hydrogen, lower alkyl, $-(CH_2)_m$-aryl,

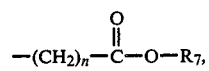

or $R_5$ and $R_6$ taken together with the N-atom to which they are attached complete a heterocyclic ring of the formula

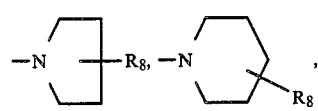

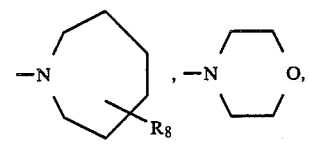

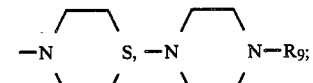

$R_7$ is hydrogen, lower alkyl, $-(CH_2)_m$-aryl, or a pharmaceutically acceptable salt forming ion;

$R_8$ is hydrogen, lower alkyl of 1 to 4 carbons, lower alkoxy of 1 to 4 carbons, lower alkylthio of 1 to 4 carbons, halo, $CF_3$ or hydroxy;

$R_9$ is hydrogen or lower alkyl;

$R_{10}$ is hydrogen, lower alkyl of 1 to 4 carbons, lower alkoxy of 1 to 4 carbons, halo, or $CF_3$;

m is zero or an integer from 1 to 6;

n is an integer from 1 to 6;

p is an integer from 2 to 6;

the term "lower alkyl" refers to straight or branched chain hydrocarbon radicals of one to eight carbons;

the term "lower alkenyl" refers to straight or branched chain hydrocarbon radicals of two to eight carbons with one double bond;

the term "lower alkynyl" refers to straight or branched chain hydrocarbon radicals of two to eight carbons with one triple bond;

the term "cycloalkyl" refers to saturated rings of 4 to 7 carbons;

the term "halo" refers to chloro, bromo, and fluoro;

the term "aryl" refers to phenyl, 1-naphthyl, 2-naphthyl, mono substituted phenyl, 1-naphthyl or 2-naphthyl wherein said substituent is lower alkyl of 1 to 4 carbons, lower alkoxy of 1 to 4 carbons, lower alkylthio of 1 to 4 carbons, halo, nitro, cyano, hydroxy, amino, —NH-alkyl wherein alkyl is of 1 to 4 carbons, —N(alkyl)$_2$ wherein alkyl is of 1 to 4 carbons, $CF_3$, NCS, $OCHF_2$,

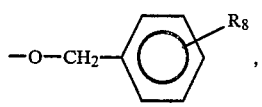

—O—$CH_2$-cycloalkyl,

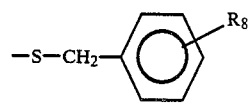

or —S—$CH_2$-cycloalkyl, di- or tri-substituted phenyl, 1-naphthyl, or 2-naphthyl wherein said substituents are selected from the group consisting of methyl, methoxy, methylthio, halo, $CF_3$, nitro, hydroxy, amino, and $OCHF_2$, and pentafluorophenyl;

the term "heterocyclo" refers to monocyclic rings selected from the group consisting of 2-thienyl, 3-thienyl, 2-furyl, 3-furyl, 2-pyridyl, 3-pyridyl, 4-pyridyl and imidazolyl, bicyclic rings selected from the group consisting of 4,5,6, or 7-indolyl, 4,5,6, or 7-isoindolyl, 5,6,7, or 8-quinolinyl, 5,6,7, or 8-isoquinolinyl, 4,5,6, or 7-benzothiazolyl, 4,5,6, or 7-benzoxazolyl, 4,5,6, or 7-benzimidazolyl, 4,5,6, or 7-benzoxadiazolyl, and 4,5,6, or 7-benzofurazanyl, and said monocyclic and bicyclic heterocyclo rings wherein an available carbon atom is substituted with lower alkyl of 1 to 4 carbons, lower alkylthio of 1 to 4 carbons, lower alkoxy of 1 to 4 carbons, halo, keto, nitro, cyano, hydroxy, amino, —NH-alkyl wherein alkyl is of 1 to 4 carbons, —N(alkyl)$_2$ wherein alkyl is of 1 to 4 carbons, $CF_3$, NCS, or $OCHF_2$ or said monocyclic and bicyclic rings wherein two or three available carbon atoms have substituents selected from the group consisting of methyl, methoxy, methylthio, halo, $CF_3$, nitro, hydroxy, amino, and $OCHF_2$.

2. A compound of claim 1 of the formula

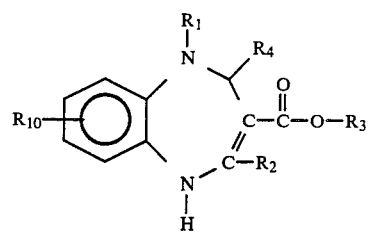

including a pharmaceutically acceptable salt thereof wherein:

$R_1$ is hydrogen or

wherein lower alkyl is straight or branched chain of 1 to 4 carbons;

$R_2$ is straight or branched chain lower alkyl of 1 to 5 carbons;

$R_3$ is straight or branched chain lower alkyl of 1 to 5 carbons, —$(CH_2)_p$—O—lower alkyl wherein lower alkyl is straight or branched chain of 1 to 5 carbons,

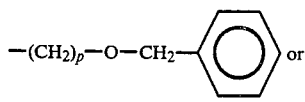

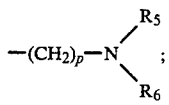

p is 2, 3 or 4;

$R_4$ is phenyl, 2-,3- or 4- mono substituted phenyl wherein said substituent is lower alkyl of 1 to 4 carbons, lower alkoxy of 1 to 4 carbons, lower alkylthio of 1 to 4 carbons, halo, $CF_3$, nitro or $OCHF_2$, 2,3-disubstituted phenyl, 2,6-disubstituted phenyl, 2,3,4-trisubstituted phenyl, or 3,4,5-trisubstituted phenyl wherein said phenyl substituents are selected from the group consisting of methyl, methoxy, methylthio, halo, $CF_3$, nitro and $OCHF_2$, or pentafluorophenyl;

$R_5$ and $R_6$ are independently selected from the group consisting of hydrogen, straight or branched chain lower alkyl of 1 to 5 carbons, and benzyl; and $R_{10}$ is hydrogen, methyl, methoxy, chloro, or $CF_3$.

3. A compound of claim 2 wherein:

$R_1$ is hydrogen or

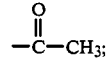

$R_2$ is methyl;

$R_3$ is methyl or ethyl;

$R_4$ is 2-nitrophenyl, 3-nitrophenyl, 2-(trifluoromethyl)phenyl, 2,3-dichlorophenyl, or 2,6-dichlorophenyl; and $R_{10}$ is hydrogen.

4. The compound of claim 3 wherein:

$R_1$ is hydrogen;

$R_3$ is methyl; and
$R_4$ is 2-nitrophenyl.

5. The compound of claim 3 wherein:
$R_1$ is hydrogen;
$R_3$ is methyl; and
$R_4$ is 3-nitrophenyl.

6. The compound of claim 3 wherein:
$R_1$ is hydrogen;
$R_3$ is methyl; and
$R_4$ is 2-(trifluoromethyl)phenyl.

7. The compound of claim 3 wherein:
$R_1$ is hydrogen;
$R_3$ is methyl; and
$R_4$ is 2,3-dichlorophenyl.

8. The compound of claim 3 wherein:
$R_1$ is hydrogen;
$R_3$ is methyl; and
$R_4$ is 2,6-dichlorophenyl.

9. The compound of claim 3 wherein:
$R_1$ is

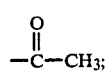

$R_3$ is methyl; and
$R_4$ is 3-nitrophenyl.

10. A composition useful in reducing blood pressure in a mammal comprising a pharmaceutically acceptable carrier and an anti-hypertensively effective amount of a compound or pharmaceutically acceptable salt thereof of the formula

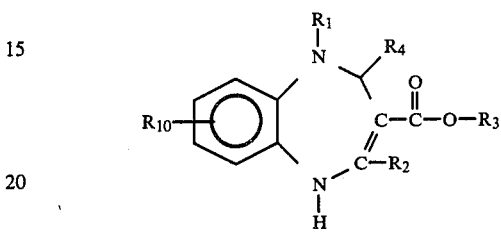

wherein $R_1$, $R_2$, $R_3$, $R_4$, and $R_{10}$ are as defined in claim 1.

11. The method of reducing blood pressure in a mammal comprising administering an effective amount of the composition of claim 10.

* * * * *